(12) United States Patent
Terasaka et al.

(10) Patent No.: US 7,968,750 B2
(45) Date of Patent: Jun. 28, 2011

(54) PROCESS FOR PRODUCING NITROGEN-CONTAINING COMPOUNDS

(75) Inventors: Michio Terasaka, Wakayama (JP); Tetsuaki Fukushima, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/676,188

(22) PCT Filed: Aug. 27, 2008

(86) PCT No.: PCT/JP2008/065783
§ 371 (c)(1),
(2), (4) Date: Mar. 3, 2010

(87) PCT Pub. No.: WO2009/031546
PCT Pub. Date: Mar. 12, 2009

(65) Prior Publication Data
US 2010/0179349 A1     Jul. 15, 2010

(30) Foreign Application Priority Data
Sep. 7, 2007   (JP) .................................. 2007-232478

(51) Int. Cl.
*C07C 209/50* (2006.01)
(52) U.S. Cl. ...................................................... 564/488
(58) Field of Classification Search ........................ None
See application file for complete search history.

(56) References Cited

U.S. PATENT DOCUMENTS

| | | | | | |
|---|---|---|---|---|---|
| 2,609,394 | A | * | 9/1952 | Davies et al. ................. | 564/479 |
| 5,075,505 | A | * | 12/1991 | Forquy et al. ................. | 564/488 |
| 2006/0287556 | A1 | | 12/2006 | Loenders et al. | |
| 2007/0191642 | A1 | * | 8/2007 | Loenders et al. ............. | 564/488 |
| 2009/0292145 | A1 | | 11/2009 | Fukushima et al. | |

FOREIGN PATENT DOCUMENTS

GB    1 206 981    9/1970

OTHER PUBLICATIONS

Database CAPLUS on STN, Acc. No. 2001:788848, Taniguchi et al., JP 2001302596 A (Oct. 31, 2001) (abstract).*
U.S. Appl. No. 12/672,327, filed Feb. 5, 2010, Terasaka, et al.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

The present invention relates to a process for producing a tertiary amine by reducing an amide compound in the presence of a catalyst containing a sponge copper catalyst obtained by leaching alloy particles containing copper and aluminum and drying the thus leached alloy particles. The present invention provides a process for producing high-purity aliphatic tertiary amines containing a less amount of by-products at a high yield by subjecting aliphatic acid amides to hydrogenation reduction under solvent-free moderate conditions.

19 Claims, No Drawings

PROCESS FOR PRODUCING NITROGEN-CONTAINING COMPOUNDS

CROSS REFERENCES TO RELATED APPLICATIONS

This application is a 371 of International Patent Application No. PCT/JP08/065783, filed on Aug. 27, 2008, and claims priority to Japanese Patent Application No. 2007-232478, filed on Sep. 7, 2007.

FIELD OF THE INVENTION

The present invention relates to a process for producing nitrogen-containing compounds, and more particularly to a process for producing high-purity aliphatic tertiary amines from aliphatic acid amides.

BACKGROUND OF THE INVENTION

Aliphatic tertiary amines are important intermediate products in domestic and industrial application fields, and have been used in extensive applications such as, for example, fabric softener, antistatic agents, additives for gasoline, shampoos, rinses, bactericides and detergents.

As the method for producing the aliphatic tertiary amines, there is known an amide reduction method in which an amide obtained from inexpensive regenerative fatty acids is used as a raw material. As the amide reduction method, there are conventionally known various methods using a cobalt-based catalyst, a noble metal-based catalyst, etc. However, any of these conventional methods inevitably require to use a solvent, resulting in problems such as poor productivity.

There is also known the method using a copper/chromium-based catalyst. For example, JP 3-500300A discloses a process for producing tertiary amines in which hydrogen and dimethylamine are flowed through and reacted with a raw amide under a pressure of from 1 to 10 MPa in a batch reactor charged with a copper/chromium/manganese catalyst. US 2006-287556A discloses a process for producing amines in which the reaction is conducted in the presence of hydrogen and an optional amine source under a pressure of from 0.2 to 5 MPa in a fixed bed reactor charged with a hydrogenation catalyst such as a copper/chromium catalyst. However, these catalysts used in the above conventional processes must be handled with great care to ensure a safety, etc., upon disposal. Therefore, there is a demand for development of chromium-free catalysts. Further, in these conventional methods in which the amide compounds are reduced by flowing a mixed gas of hydrogen and the amine source (dimethylamine) therethrough, there are still present problems to be improved, such as a poor selectivity to the aimed tertiary amines in the method described in JP 3-500300A, and need of flowing a large excess amount of hydrogen through the raw amide in the method described in US 2006-287556A.

There is also disclosed a method for producing tertiary amines in which an amide compound is reduced in a hydrogen atmosphere using the other copper-based catalyst such as a copper/zinc catalyst, a copper/zinc/ruthenium catalyst and a copper/nickel/ruthenium catalyst (refer to JP 2001-302596A). However, this method is still unsatisfactory because of occurrence of a large amount of by-products such as alcohols. Further, there is disclosed a method for producing linear tertiary amines by using granular Raney copper catalysts or granular Raney cobalt catalysts (JP 62-51646A). However, the starting material used in the above method is an alcohol. Therefore, it is not conventionally known whether the sponge copper-based catalysts are useful in techniques for producing tertiary amines from amide compounds.

SUMMARY OF THE INVENTION

The present invention relates to a process for producing a tertiary amine represented by the following general formula (2):

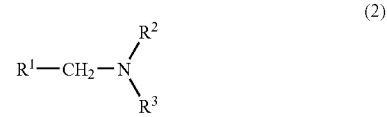

wherein $R^1$ is a linear or branched aliphatic hydrocarbon group having 5 to 23 carbon atoms; and $R^2$ and $R^3$ are respectively a linear or branched alkyl group having 1 to 6 carbon atoms and may be the same or different, said process including the step of (a) reducing an amide compound represented by the following general formula (1):

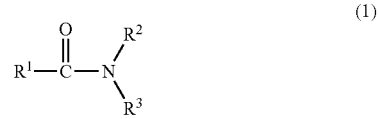

wherein $R^1$, $R^2$ and $R^3$ are the same as defined above, in the presence of a sponge copper catalyst obtained by leaching alloy particles containing copper and aluminum and drying the thus leached alloy particles.

DETAILED DESCRIPTION OF THE INVENTION

The present invention provides a process for producing high-purity aliphatic tertiary amines containing a less amount of by-products with a high yield by subjecting aliphatic acid amides to hydrogenation reduction in the presence of a chromium-free copper-based catalyst under solvent-free moderate conditions.

The process for producing a tertiary amine according to the present invention includes the step of (a) reducing an amide compound represented by the above general formula (1) in the presence of a sponge copper catalyst obtained by leaching alloy particles containing copper and aluminum and then drying the thus leached alloy particles.

In each of the above general formulae (1) and (2), $R^1$ represents a linear or branched aliphatic hydrocarbon group having 5 to 23 carbon atoms. Meanwhile, the branched aliphatic hydrocarbon group also includes an alicyclic group. In addition, the aliphatic hydrocarbon group may be either saturated or unsaturated.

$R^1$ is preferably a linear or branched alkyl group or alkenyl group having 5 to 21 carbon atoms and more preferably 7 to 21 carbon atoms, from the viewpoint of usefulness of the resultant tertiary amine. Specific examples of the alkyl or alkenyl group as $R^1$ include various heptyl groups, various octyl groups, various nonyl groups, various decyl groups, various undecyl groups, various dodecyl groups, various tridecyl groups, various tetradecyl groups, various pentadecyl groups, various hexadecyl groups, various heptadecyl groups, various octadecyl groups, various nonadecyl groups, various eicosanyl groups, various heneicosanyl groups, various tricosanyl groups, various heptenyl groups, various octenyl groups, various nonenyl groups, various decenyl groups, various undecenyl groups, various dodecenyl groups, various tridecenyl groups, various tetradecenyl groups, various pentadecenyl groups, various hexadecenyl groups, various heptadecenyl groups, various octadecenyl groups, various nonadecenyl groups, various icosenyl groups, various heneicosenyl groups and various behenyl groups. Among these groups, preferred are various heptyl groups, various nonyl groups, various undecyl groups, various tridecyl groups, various pentadecyl groups, various heptadecyl groups, various nonadecyl groups, various heneicosanyl groups, various heptenyl groups, various nonenyl groups, various undecenyl groups, various tridecenyl groups, various pentadecenyl groups, various heptadecenyl groups, various nonadecenyl groups and various heneicosenyl groups. The term "various" used herein means all of those groups having a linear chain or a branched chain.

In each of the above general formulae (1) and (2), $R^2$ and $R^3$ are each independently a linear or branched alkyl group having 1 to 6 carbon atoms. Meanwhile, the "branched alkyl group" also includes a cycloalkyl group. Examples of $R^2$ and $R^3$ respectively include methyl, ethyl, n-propyl, isopropyl, n-butyl, isobutyl, sec-butyl, tert-butyl, various pentyl groups, various hexyl groups, cyclopentyl and cyclohexyl. Among these groups, preferred are methyl, ethyl and propyl from the viewpoint of usefulness of the resultant tertiary amine. $R^2$ and $R^3$ may be the same or different.

Examples of the amide compound represented by the above general formula (1) include N,N-dimethyl aliphatic acid amides such as N,N-dimethyl caprylamide, N,N-dimethyl 2-ethylhexane amide, N,N-dimethyl caprinamide, N,N-dimethyl lauroyl amide, N,N-dimethyl myristoyl amide, N,N-dimethyl palmitoyl amide, N,N-dimethyl stearoyl amide, N,N-dimethyl isostearoyl amide, N,N-dimethyl oleyl amide and N,N-dimethyl behenyl amide; and compounds obtained by replacing the N,N-dimethyl group of these aliphatic acid amides with N,N-diethyl, N,N-dipropyl, N-ethyl-N-methyl, N-methyl-N-propyl or N-ethyl-N-propyl.

On the other hand, examples of the tertiary amine represented by the above general formula (2) include amine compounds corresponding to the above exemplified amide compounds of the general formula (1). Specific examples of the tertiary amine include N,N-dimethyl aliphatic amines such as N,N-dimethyl octyl amine, N,N-dimethyl 2-ethylhexyl amine, N,N-dimethyl decyl amine, N,N-dimethyl lauryl amine, N,N-dimethyl myristyl amine, N,N-dimethyl hexadecyl amine, N,N-dimethyl stearyl amine, N,N-dimethyl isostearyl amine, N,N-dimethyl oleyl amine and N,N-dimethyl behenyl amine; and compounds obtained by replacing the N,N-dimethyl group of these aliphatic amines with N,N-diethyl, N,N-dipropyl, N-methyl-N-propyl, N-ethyl-N-methyl, N-methyl-N-propyl or N-ethyl-N-propyl.

The catalyst used in the process for producing the tertiary amine according to the present invention contains a sponge copper catalyst obtained by leaching alloy particles containing copper and aluminum and then drying the thus leached alloy particles. A part of the aluminum in the sponge copper catalyst may be replaced with silicon. Also, the catalyst preferably contains, in addition to copper and aluminum, at least one element selected from the group consisting of zinc, molybdenum, manganese, magnesium, iron, ruthenium and vanadium from the viewpoints of a good activity and a good selectivity of the resultant catalyst. The sponge copper catalyst is more preferably obtained by leaching the alloy particles and then drying the thus leached alloy particles in an atmosphere of oxygen or air from the viewpoints of a good activity and a good selectivity of the resultant catalyst.

In general, the "sponge catalyst" is formerly called "Raney catalyst", and the definition and general production methods thereof are described in "15107 Chemical Products" published by The Chemical Daily Co., Ltd. The "sponge catalyst" used in the present invention includes those catalysts obtained by leaching the above alloy particles and then drying the thus leached alloy particles. The "leaching" used herein means such a procedure in which catalytically inactive portions (aluminum or silicon contained in the alloy) are eluted out with an alkali from the above alloy particles to allow the alloy particles to exhibit a good catalytic activity. With the leaching procedure, it is possible to obtain a catalyst having a large specific surface area.

The alloy particles contain at least copper and aluminum. The mass ratio of aluminum to copper (aluminum/copper) in the alloy particles is preferably from 0.2 to 6.0, more preferably from 0.3 to 2.5 and still more preferably from 0.4 to 1.5 from the viewpoints of good activity, selectivity and durability of the resultant catalyst.

In the present invention, the sponge copper catalyst preferably contains, in addition to copper and aluminum, other elements as a co-catalyst from the viewpoints of a good activity and a good selectivity of the resultant catalyst. As the co-catalyst, preferred is at least one element selected from the group consisting of zinc, molybdenum, manganese, magnesium, iron, ruthenium and vanadium, and more preferred is at least one element selected from the group consisting of zinc, magnesium, iron and vanadium. The sponge copper catalyst more preferably contains copper, aluminum and zinc, and still more preferably contains copper, aluminum, zinc and magnesium. Thus, the alloy particles used in the present invention preferably further contain the metal component acting as a co-catalyst and more preferably at least one element selected from the group consisting of zinc, magnesium, iron and vanadium. Specifically, the alloy particles are still more preferably composed of copper, aluminum and zinc, and further still more preferably composed of copper, aluminum, zinc and magnesium.

Thus, the sponge copper catalyst is obtained by leaching and then drying the above alloy particles. The leaching treatment may be specifically carried out by suspending the alloy particles in water and dissolving the alloy particles therein with an alkali, etc., to thereby elute out catalytically inactive portions therefrom.

Examples of the alkali used in the leaching treatment include sodium hydroxide, lithium hydroxide, potassium hydroxide, rubidium hydroxide and cesium hydroxide. Among these alkalis, from the viewpoint of low production costs, preferred are sodium hydroxide and potassium hydroxide. These alkalis may be used in the form of an aqueous solution. The amount of the alkali used in the leaching treatment is preferably from 0.1 to 4 mol and more preferably from 0.5 to 3 mol per 1 mol of the metals to be eluted out with the alkali such as aluminum and silicon. The proportion of the metals such as aluminum which are eluted and dissolved out with the alkali from the alloy particles is preferably from 40 to 99.9% by mass and more preferably from 50 to 99.5% by mass on the basis of the metals such as aluminum which are contained in the alloy.

The temperature used upon the leaching treatment is not particularly limited as long as the metals such as aluminum are dissolved in the alkali. From the viewpoint of a good dissolvability of the metals such as aluminum, the leaching temperature is preferably from room temperature to 100° C. and more preferably from 40 to 95° C.

In the present invention, after the leaching but before the drying, the thus leached alloy particles may be optionally aged under given conditions for the purpose of controlling the amount of residual catalytically inactive portions such as aluminum therein. Further, the leached alloy particles may also be optionally subjected to washing with water and/or filtration in order to remove unreacted alkali or reaction products of the alkali with aluminum, etc., therefrom.

The sponge copper catalyst used in the present invention is obtained by drying the leached alloy particles. The drying of the leached particles is preferably carried out in an atmosphere of oxygen or air in order to oxidize a surface of the respective metals contained therein from the viewpoints of good activity, selectivity and durability of the resultant catalyst. The drying temperature is preferably from 60 to 500° C. and more preferably from 100 to 400° C. from the viewpoints of good activity, selectivity and durability of the resultant catalyst.

The sponge copper catalyst used in the present invention may be obtained, for example, by suspending the above alloy particles in ion-exchanged water, adding the above aqueous alkali solution to the resultant suspension to leach the alloy particles under given conditions, and then after optionally subjecting the leached particles to aging, washing with water and/or filtration, drying the resultant particles at a desired temperature under an air flow.

The sponge copper catalyst used in the present invention preferably contains copper in an amount of from 20 to 90% by mass, more preferably from 30 to 85% by mass and still more preferably from 35 to 85% by mass in terms of metallic copper from the viewpoints of good activity, selectivity and durability of the resultant catalyst. In addition, the mass ratio of aluminum to copper (aluminum/copper) in the sponge copper catalyst is preferably from 0.003 to 0.8, more preferably from 0.005 to 0.7 and still more preferably from 0.007 to 0.7 from the viewpoints of good activity, selectivity and durability of the resultant catalyst. Further, the sponge copper catalyst used in the present invention is preferably capable of satisfying both the ranges of the copper content and the mass ratio of aluminum/copper.

The thus obtained sponge copper catalyst used in the present invention may also contain the elements other than copper as a co-catalyst as described previously.

In the present invention, as described above, upon production of the catalyst, the co-catalyst may be previously included in the alloy particles containing copper and aluminum. Alternatively, the co-catalyst may be added separately from the alloy particles containing copper and aluminum. In the present invention, from the same viewpoints as described above, there is preferably used such a sponge copper catalyst obtained by leaching the alloy particles containing copper, aluminum and zinc and then calcining the thus leached alloy particles.

The content of the co-catalyst in the sponge copper catalyst is controlled from the viewpoints of a good activity and a good selectivity of the resultant catalyst such that the mass ratio of the co-catalyst to copper (co-catalyst/copper) is preferably from 0.002 to 0.8, more preferably from 0.003 to 0.6 and still more preferably from 0.003 to 0.5.

The contents of the respective metal elements in the sponge copper catalyst may be quantitatively determined using a wavelength dispersive fluorescent X-ray analyzer. More specifically, 5 g of lithium tetraborate and a stripping agent ($LiCO_3$:$LiBr$:$LiNO_3$=5:1:5) are added to 0.1 g of a sample containing the respective metal elements, and the resultant mixture is fused with an alkali at 1050° C. to prepare glass beads thereof. The thus prepared glass beads are evaluated using a wavelength dispersive fluorescent X-ray analyzer "ZSX100e" available from Rigaku Corporation. The measured X-ray intensity values of the respective metal elements in the sample are compared with those in a calibration curve of a control sample prepared by mixing high-purity samples of the respective metal elements at aimed concentrations, thereby determining the contents of the respective metal element in the sample.

Also, the contents of the platinum-group elements in the catalyst is determined as follows. That is, 0.5 g of a sample is charged together with ammonium hydrogensulfate in an amount several ten times the amount of the sample, into a testing tube made of a hard glass, and decomposed under heating. Then, the resultant decomposed product is dissolved in water under heating, and the obtained solution is subjected to ICP emission spectrometry to measure the contents of the platinum-group elements in the solution.

The process for producing the tertiary amine according to the present invention includes the step of (a) reducing the amide compound represented by the general formula (1) in a hydrogen atmosphere in the presence of the thus produced catalyst (step(a)). In the followings, the process for producing the tertiary amine according to the present invention is explained in detail.

In the present invention, the amide represented by the general formula (1) is subjected to hydrogenation reduction in the presence of the above-prepared catalyst.

The amide hydrogenation-reduction is usually conducted under solvent-free condition from the viewpoints of enhancing the productivity and reducing the burden of production facilities, and may be carried out in a hydrogen atmosphere under normal pressures or under a hydrogen-applied pressure, or in a flowing hydrogen under normal pressures or under applied pressure. The reaction may be conducted by either a continuous method or a batch method. In the batch method, the amount of the catalyst used is preferably from 0.1 to 20% by mass, more preferably from 0.5 to 15% by mass and still more preferably from 1 to 10% by mass in terms of the sponge copper catalyst on the basis of the amide compound represented by the general formula (1) from the viewpoints of a good reactivity, a good selectivity and low production costs. The catalyst used in the present invention may be recovered after completion of the reaction and then reused from the viewpoint of reducing the production costs.

The reaction temperature is usually from about 140 to about 300° C., preferably from 160 to 280° C. and still more preferably from 180 to 270° C. from the viewpoints of enhancing the reaction rate and suppressing production of by-products. The amount of hydrogen flowed through the reaction system is preferably from 0.1 to 15 mol/h, more preferably from 0.3 to 10 mol/h and still more preferably from 0.5 to 5 mol/h per 1 mol of the amide compound represented by the general formula (1) from the viewpoints of attaining a good reactivity, suppressing production of by-products and facilitating removal of water produced. The reaction pressure is usually from normal pressures to about 25 MPaG (G: gauge pressure), preferably from 0.1 to 10 MPaG and more preferably from 0.1 to 5 MPaG from the viewpoints of enhancing the reaction rate and suppressing increase in burden of facilities.

The amide hydrogenation reduction is preferably carried out while removing water produced by the reaction from the viewpoint of promoting the reaction. As the method of removing water produced by the reaction, there may be used any of a method of purging the water out of the reaction system by flowing hydrogen or a mixed gas composed of hydrogen and an inert gas therethrough as described above, an azeotropic method, an ordinary dehydration method, etc. Thus, when subjecting the amide represented by the general formula (1)

to hydrogenation reduction under the solvent-free moderate conditions, the high-purity tertiary amine represented by the general formula (2) which contains a less amount of by-products can be produced with a high yield.

In the present invention, from the viewpoint of enhancing the purity of the tertiary amine obtained in the step (a) with a still higher selectivity, it is preferred that a dialkyl amine containing a linear or branched alkyl group having 1 to 6 carbon atoms and hydrogen are further introduced into the reaction system in the presence of a catalyst (hereinafter occasionally referred to a "step (b)"). In the present invention, as the catalyst present in the step (b), there is preferably used the sponge copper catalyst used in the step (a) from the viewpoints of a good productivity and low production costs.

In the step (b), the dialkyl amine containing a linear or branched alkyl group having 1 to 6 carbon atoms is further introduced into the reaction system to treat the reaction product obtained above therewith. Incidentally, in the step (a), an alcohol is by-produced together with the tertiary amine as the aimed product. The alcohol has a boiling point close to that of the aimed tertiary amine, and are therefore hardly separated from the tertiary amine by distillation, etc. For this reason, in the step (b), in order to further increase a purity of the tertiary amine, the dialkyl amine containing a linear or branched alkyl group having 1 to 6 carbon atoms is introduced to the reaction system to thereby convert the alcohol into a dialkyl tertiary amine. The transfer of the step (a) to the step (b) is preferably conducted when the amount of the raw amide compound used in the step (a) is reduced to 5% by mass or less and more preferably when reduced to 1% by mass or less as measured by gas chromatography, from the viewpoints of a good productivity and a less production of the by-products.

Examples of the linear or branched alkyl group having 1 to 6 carbon atoms which is contained in the dialkyl amine used in the step (b) include those alkyl groups respectively exemplified as each of $R^2$ and $R^3$ in the general formula (1) or (2). Among these alkyl groups, from the viewpoint of usefulness of the resultant tertiary amine, preferred are methyl, ethyl and propyl.

The step (b) may be carried out in a hydrogen atmosphere under normal pressures or under hydrogen-applied pressure, or in a flowing hydrogen under normal pressures or under applied pressure. The flowing amount of the dialkyl amine is preferably from 0.001 to 1 mol/h, more preferably from 0.005 to 0.5 mol/h and still more preferably from 0.01 to 0.3 mol/h per 1 mol of the raw amide compound from the viewpoints of a good reactivity and a less production of the by-products.

The treating temperature of the step (b) is preferably from 140 to 270° C., more preferably from 160 to 260° C. and still more preferably from 180 to 250° C. from the viewpoints of a good reactivity and a less production of the by-products. Also, the flowing amount of hydrogen in the step (b) is preferably from 0.1 to 15 mol/h, more preferably from 0.3 to 10 mol/h and still more preferably from 0.5 to 5 mol/h per 1 mol of the raw amide compound from the viewpoints of a good reactivity, a less production of the by-products and facilitated removal of water produced by the reaction. The treating pressure of the step (b) is preferably from normal pressures to 15 MPaG, more preferably from normal pressures to 5 MPaG and still more preferably from normal pressures to 3 MPaG from the viewpoints of enhancing the reaction rate and suppressing increase in load of facilities.

With the provision of the above step (b), since the suitable reaction conditions which are different from those of the step (a) can be selected therefor, the purity of the tertiary amine obtained in the step (a) by hydrogenation-reducing the aliphatic acid amide under the moderate conditions can be further increased. As a result, the aliphatic tertiary amine containing a less amount of the by-products and having a higher purity can be produced with a high yield.

In accordance with the process of the present invention in which the aliphatic acid amide is subjected to hydrogenation reduction under the solvent-free moderate conditions, it is possible to produce the high-purity aliphatic tertiary amine containing a less amount of by-products with a high yield. In addition, since the catalyst used in the process is a chromium-free catalyst, the disposal treatment for the used catalyst can be carried out with a high safety.

In the process for producing the tertiary amine according to the present invention, the high-purity aliphatic tertiary amine containing a less amount of by-products can be produced. The aliphatic tertiary amine produced according to the process of the present invention is an important intermediate product in domestic and industrial application fields, and can be suitably used in extensive applications such as, for example, fabric softener, antistatic agents, additives for gasoline, shampoos, rinses, bactericides and detergents.

The present invention is described in more detail by referring to the following examples, etc. However, it should be noted that these examples, etc., are only illustrative and not intended to limit the invention thereto.

Meanwhile, in the following Production Examples, the contents of the respective metals except for Ru in the catalyst were measured using a wavelength dispersive fluorescent X-ray analyzer "ZSX100e" available from Rigaku Corporation, and the content of Ru in the catalyst was measured using a ICP emission spectrometric analyzer "JY238" available from Jobin Ybon Corp., according to the above-mentioned methods. Also, the analysis of composition of the respective reaction products by gas chromatography was carried out using the following apparatus.

Gas Chromatograph: "HEWLETT PACKARD Series 6890"

Column: "DB-17" available from J & W Corp. (inner diameter×length×film thickness: 15 m×0.25 m×0.5 μm)

Catalyst Production Example 1

Thirty grams of Cu/Al alloy particles [Al/Cu (mass ratio): 1.0; particle size: 150 μm or less (particles passed through a 100 mesh powder sieve were used; this is similarly applied to the subsequent descriptions)] were suspended in 300 mL of ion-exchanged water, and the resultant suspension was heated to 80° C. while stirring. After reaching the given temperature, a 25 mass % NaOH aqueous solution was dropped to the suspension in such an amount that the amount of NaOH added was 2 mol per 1 mol of Al contained in the alloy particles. After completion of the dropping, the resultant mixture was aged at the same temperature for 2 h to leach the alloy particles. Next, the reaction mixture was subjected to washing with water (decantation) and filtration, and the obtained leached particles were dried at 300° C. in air, thereby obtaining a sponge copper catalyst A. As a result, it was confirmed that the thus obtained sponge copper catalyst A had a Cu content of 79.5% by mass and an Al content of 0.8% by mass (Al/Cu (mass ratio): 0.01) in terms of the respective metal elements.

Catalyst Production Example 2

The same procedure as in Catalyst Production Example 1 was repeated except for using 30 g of Cu/Zn/Al alloy particles (Al/Cu (mass ratio): 1.1; Zn/Cu (mass ratio): 0.1; particle size: 150 μm or less) in place of the Cu/Al alloy particles, thereby obtaining a sponge copper catalyst B. As a result, it was confirmed that the thus obtained sponge copper catalyst B had a Cu content of 74.0% by mass, a Zn content of 7.1% by mass and an Al content of 0.6% by mass (Al/Cu (mass ratio): 0.008; Zn/Cu (mass ratio): 0.1) in terms of the respective metal elements.

Catalyst Production Example 3

The same procedure as in Catalyst Production Example 1 was repeated except for using 30 g of Cu/Zn/Mg/Al alloy particles (Al/Cu (mass ratio): 1.18; Zn/Cu (mass ratio): 0.04; Mg/Cu (mass ratio): 0.007; particle size: 15 µm or less) in place of the Cu/Al alloy particles, thereby obtaining a sponge copper catalyst C. As a result, it was confirmed that the thus obtained sponge copper catalyst C had a Cu content of 73.4% by mass, a Zn content of 3.2% by mass, a Mg content of 0.5% by mass and an Al content of 0.9% by mass (Al/Cu (mass ratio): 0.01; Zn/Cu (mass ratio): 0.04; Mg/Cu (mass ratio): 0.007) in terms of the respective metal elements.

Catalyst Production Example 4

The same procedure as in Catalyst Production Example 3 was repeated except that 30 g of Cu/Zn/Mg/Al alloy particles having a different composition from that of Catalyst Production Example 3 (Al/Cu (mass ratio): 1.24; Zn/Cu (mass ratio): 0.23; Mg/Cu (mass ratio): 0.006; particle size: 150 µm or less) were used, the 25 mass % NaOH aqueous solution was added in such an amount that the amount of NaOH added was 1.5 mol per 1 mol of Al contained in the alloy particles, and the leaching treatment was conducted at 70° C., thereby obtaining a sponge copper catalyst D. As a result, it was confirmed that the thus obtained sponge copper catalyst D had a Cu content of 51.9% by mass, a Zn content of 11.9% by mass, a Mg content of 0.3% by mass and an Al content of 10.8% by mass (Al/Cu (mass ratio): 0.21; Zn/Cu (mass ratio): 0.23; Mg/Cu (mass ratio): 0.006) in terms of the respective metal elements.

Catalyst Production Example 5

The same procedure as in Catalyst Production Example 4 was repeated except that the leaching treatment was conducted at 80° C., thereby obtaining a sponge copper catalyst E. As a result, it was confirmed that the thus obtained sponge copper catalyst E had a Cu content of 56.6% by mass, a Zn content of 13.8% by mass, a Mg content of 0.3% by mass and an Al content of 4.4% by mass (Al/Cu (mass ratio): 0.08; Zn/Cu (mass ratio): 0.23; Mg/Cu (mass ratio): 0.005) in terms of the respective metal elements.

Catalyst Production Example 6

The same procedure as in Catalyst Production Example 3 was repeated except that 30 g of Cu/Zn/Mg/Al alloy particles having a different composition from that of Catalyst Production Example 3 (Al/Cu (mass ratio): 1.33; Zn/Cu (mass ratio): 0.3; Mg/Cu (mass ratio): 0.03; particle size: 150 µm or less) were used, and the 25 mass % NaOH aqueous solution was added in an such amount that the amount of NaOH added was 1.3 mol per 1 mol of Al contained in the alloy particles, thereby obtaining a sponge copper catalyst F. As a result, it was confirmed that the thus obtained sponge copper catalyst F had a Cu content of 43.3% by mass, a Zn content of 13.1% by mass, a Mg content of 1.3% by mass and an Al content of 16.7% by mass (Al/Cu (mass ratio): 0.39; Zn/Cu (mass ratio): 0.3; Mg/Cu (mass ratio): 0.03) in terms of the respective metal elements.

Catalyst Production Example 7

The same procedure as in Catalyst Production Example 1 was repeated except that 30 g of Cu/Zn/Ru/Al alloy particles (Al/Cu (mass ratio): 1.02; Zn/Cu (mass ratio): 0.02; Ru/Cu (mass ratio): 0.004; particle size: 150 µm or less) were used in place of the Cu/Al alloy particles, and a 15 mass % NaOH aqueous solution was used in place of the 25 mass % NaOH aqueous solution, thereby obtaining a sponge copper catalyst G. As a result, it was confirmed that the thus obtained sponge copper catalyst G had a Cu content of 79.0% by mass, a Zn content of 1.4% by mass, a Ru content of 0.3% by mass and an Al content of 1.2% by mass (Al/Cu (mass ratio): 0.02; Zn/Cu (mass ratio): 0.02; Ru/Cu (mass ratio): 0.004) in terms of the respective metal elements.

Catalyst Production Example 8

The same procedure as in Catalyst Production Example 1 was repeated except that 30 g of Cu/Zn/Mo/Mn/Al alloy particles (Al/Cu (mass ratio): 1.19; Zn/Cu (mass ratio): 0.03; Mo/Cu (mass ratio): 0.01; Mn/Cu (mass ratio): 0.01; particle size: 150 µm or less) were used in place of the Cu/Al alloy particles, thereby obtaining a sponge copper catalyst H. As a result, it was confirmed that the thus obtained sponge copper catalyst H had a Cu content of 74.6% by mass, a Zn content of 2.6% by mass, a Mo content of 0.9% by mass, a Mn content of 0.9% by mass and an Al content of 0.7% by mass (Al/Cu (mass ratio): 0.009; Zn/Cu (mass ratio): 0.04; Mo/Cu (mass ratio): 0.01; Mn/Cu (mass ratio): 0.01) in terms of the respective metal elements.

Catalyst Production Example 9

The same procedure as in Catalyst Production Example 1 was repeated except that 30 g of Cu/Zn/V/Al alloy particles (Al/Cu (mass ratio): 1.19; Zn/Cu (mass ratio): 0.04; V/Cu (mass ratio): 0.01; particle size: 150 µm or less) were used in place of the Cu/Al alloy particles, thereby obtaining a sponge copper catalyst I. As a result, it was confirmed that the thus obtained sponge copper catalyst I had a Cu content of 71.3% by mass, a Zn content of 2.9% by mass, a V content of 1.0% by mass and an Al content of 1.1% by mass (Al/Cu (mass ratio): 0.02; Zn/Cu (mass ratio): 0.04; V/Cu (mass ratio): 0.01) in terms of the respective metal elements.

Catalyst Production Example 10

The same procedure as in Catalyst Production Example 1 was repeated except that 30 g of Cu/Fe/Al alloy particles (Al/Cu (mass ratio): 1.12; Fe/Cu (mass ratio): 0.13; particle size: 150 µm or less) were used in place of the Cu/Al alloy particles, and the obtained leached particles were dried at 400° C. in air, thereby obtaining a sponge copper catalyst J. As a result, it was confirmed that the thus obtained sponge copper catalyst J had a Cu content of 56.6% by mass, a Fe content of 7.1% by mass and an Al content of 1.0% by mass (Al/Cu (mass ratio): 0.02; Fe/Cu (mass ratio): 0.13) in terms of the respective metal elements.

Catalyst Production Example 11

The same procedure as in Catalyst Production Example 1 was repeated except that 30 g of Cu/Mg/Fe/Al alloy particles (Al/Cu (mass ratio): 1.09; Mg/Cu (mass ratio): 0.007; Fe/Cu (mass ratio): 0.08; particle size: 150 μm or less) were used in place of the Cu/Al alloy particles, thereby obtaining a sponge copper catalyst K. As a result, it was confirmed that the thus obtained sponge copper catalyst K had a Cu content of 73.4% by mass, a Mg content of 0.5% by mass, a Fe content of 5.7% by mass and an Al content of 0.9% by mass (Al/Cu (mass ratio): 0.01; Mg/Cu (mass ratio): 0.007; Fe/Cu (mass ratio): 0.08) in terms of the respective metal elements.

Meanwhile, in the metal composition of any of the catalysts produced in the above Catalyst Production Examples 1 to 11, the value obtained by subtracting a sum of mass percentages of the respective metal elements from 100 corresponds to mass % of oxygen contained therein.

Comparative Catalyst Production Example 1

Thirty grams of Cu/Al alloy particles (Al/Cu (mass ratio): 1.0; particle size: 150 μm or less) were suspended in 300 mL of ion-exchanged water, and the resultant suspension was heated to 80° C. while stirring. After reaching the given temperature, a 25 mass % NaOH aqueous solution was dropped to the suspension in such an amount that the amount of NaOH added was 1.8 mol per 1 mol of Al contained in the alloy particles. After completion of the dropping, the resultant mixture was aged at the same temperature for 2 h to leach the alloy particles. Next, the reaction mixture was washed with water (decantation), thereby obtaining a catalyst L in the form of a water suspension. As a result, it was confirmed that the thus obtained catalyst L had a Cu content of 93.0% by mass and an Al content of 3.0% by mass (Al/Cu (mass ratio): 0.03) in terms of the respective metal elements.

Comparative Catalyst Production Example 2

The same procedure as in Comparative Catalyst Production Example 1 was repeated except that Cu/Mo/Al alloy particles (Al/Cu (mass ratio): 0.82; Mo/Cu (mass ratio): 0.001; particle size: 150 μm or less) were used in place of the Cu/Al alloy particles, and the leaching treatment was conducted at 70° C., thereby obtaining a catalyst M in the form of a water suspension. As a result, it was confirmed that the thus obtained catalyst M had a Cu content of 92.0% by mass, a Mo content of 0.1% by mass and an Al content of 2.0% by mass (Al/Cu (mass ratio): 0.02; Mo/Cu (mass ratio): 0.001) in terms of the respective metal elements.

Examples 1 to 10 and Comparative Examples 1 and 2

A rotary autoclave was charged with 300 g of N,N-dimethyl lauroyl amide and 5% by mass of each of the catalysts A to J and catalysts L and M respectively produced in Catalyst Production Examples 1 to 10 and Comparative Catalyst Production Examples 1 and 2 (on the basis of the raw amide compound). An inside of the autoclave was purged with nitrogen, and then hydrogen was introduced thereinto until an inside pressure of the autoclave was increased to 1.5 MPaG. Thereafter, while maintaining the inside pressure of the autoclave at 1.5 MPaG, hydrogen was introduced into the reaction system at a rate of 40 L/h (1.35 mol/h per 1 mol of the raw amide compound). Next, the obtained reaction mixture was heated to 250° C. at which the hydrogen reduction thereof was carried out. The thus obtained reaction product was subjected to filtration to remove the catalyst therefrom. Then, the thus separated reaction solution was analyzed by gas chromatography to measure the content of the raw amide therein and the composition thereof with the passage of time, thereby calculating a reaction rate at the time at which 6 hours elapsed from initiation of the reaction and an amount (mass %) of N,N-dimethyl lauryl amine produced when the amount of the raw amide was reduced to 5%. The results are shown in Table 1. Meanwhile, the catalysts L and M both suffered from considerable deterioration in activity owing to occurrence of sintering during the reaction, so that the reaction was stopped in mid course and, therefore, failed to be completed.

Example 11

The same procedure as in Example 1 was repeated except that 300 g of N,N-dimethyl stearoyl amide was used in place of 300 g of N,N-dimethyl lauroyl amide, and the catalyst K was used in place of the catalyst A. The thus obtained reaction product was subjected to filtration to remove the catalyst therefrom. Then, the thus separated reaction solution was analyzed by gas chromatography to measure the content of the raw amide therein and the composition thereof with the passage of time, thereby calculating the reaction rate and the amount (mass %) of N,N-dimethyl stearyl amine produced. The results are shown in Table 1.

TABLE 1

| | Catalyst | Reaction rate [×10$^{-2}$ mol/(kg · H)] | Amount produced (mass %) |
|---|---|---|---|
| Example 1 | A | 39.6 | 84.9 |
| Example 2 | B | 43.6 | 83.5 |
| Example 3 | C | 51.1 | 82.5 |
| Example 4 | D | 56.8 | 79.9 |
| Example 5 | E | 55.9 | 82.9 |
| Example 6 | F | 40.1 | 81.9 |
| Example 7 | G | 40.1 | 81.2 |
| Example 8 | H | 46.3 | 85.1 |
| Example 9 | I | 65.6 | 81.1 |
| Example 10 | J | 52.0 | 81.0 |
| Example 11 | K | 39.6 | 81.7 |
| Comparative Example 1 | L | >66*[1] | — |
| Comparative Example 2 | M | >66*[1] | — |

Note
*[1]The reaction was stopped in mid course owing to occurrence of sintering on the catalyst.

Example 12

The procedure was conducted in the same manner as in Example 2. After confirming that the amount of the raw amide contained in the reaction product as measured by gas chromatography was reduced to 0.5% by mass, successively, while maintaining the same reaction temperature and pressure as well as the same hydrogen introduction rate, dimethyl amine was additionally introduced to the reaction system at a rate of 2 to 1 L/h (from 0.07 to 0.03 mol/h per 1 mol of the raw amide compound), and the resultant mixture was reacted for 3 h. The thus obtained reaction product was subjected to filtration to remove the catalyst therefrom, and then the composition of the thus separated reaction solution was analyzed by gas chromatography. The results are shown in Table 2. Meanwhile, as a result of analyzing the reaction product by gas chromatography, it was confirmed that the content of the raw amide therein was reduced below the lower detection limit.

Example 13

The procedure was conducted in the same manner as in Example 3. After confirming that the amount of the raw amide contained in the reaction product as measured by gas chromatography was reduced to the lower detection limit, successively, while maintaining the same hydrogen introduction rate of 40 L/h (1.35 mol/h per 1 mol of the raw amide compound) but changing the reaction temperature and pressure to 220° C. and normal pressures, respectively, dimethyl amine was additionally introduced to the reaction system at a rate of 6 to 4 L/h (from 0.20 to 0.14 mol/h per 1 mol of the raw amide compound), and the resultant mixture was reacted for 3 h. The thus obtained reaction product was subjected to filtration to remove the catalyst therefrom, and then the composition of the thus separated reaction solution was analyzed by gas chromatography. The results are shown in Table 2.

Example 14

The procedure was conducted in the same manner as in Example 5. After confirming that the amount of the raw amide contained in the reaction product as measured by gas chromatography was reduced to 0.6% by mass, successively, while maintaining the same temperature of 250° C. and the same hydrogen introduction rate of 40 L/h (1.35 mol/h per 1 mol of the raw amide compound) but changing the reaction pressure to 0.5 MPaG, dimethyl amine was additionally introduced to the reaction system at a rate of 2 to 1 L/h (from 0.07 to 0.03 mol/h per 1 mol of the raw amide compound), and the resultant mixture was reacted for 2 h. The thus obtained reaction product was subjected to filtration to remove the catalyst therefrom, and then the composition of the thus separated reaction solution was analyzed by gas chromatography. The results are shown in Table 2. Meanwhile, as a result of analyzing the reaction product by gas chromatography, it was confirmed that the content of the raw amide therein was reduced below the lower detection limit.

Example 15

The procedure was conducted in the same manner as in Example 8. After confirming that the amount of the raw amide contained in the reaction product as measured by gas chromatography was reduced below the lower detection limit, while maintaining the same reaction temperature of 250° C. and the same hydrogen introduction rate of 40 L/h (1.35 mol/h per 1 mol of the raw amide compound) but changing the reaction pressure to normal pressures, dimethyl amine was additionally introduced to the reaction system at a rate of 9 to 8 L/h (from 0.30 to 0.27 mol/h per 1 mol of the raw amide compound), and the resultant mixture was reacted for 2 h. The thus obtained reaction product was subjected to filtration to remove the catalyst therefrom, and then the composition of the thus separated reaction solution was analyzed by gas chromatography. The results are shown in Table 2.

Example 16

The procedure was conducted in the same manner as in Example 9. After confirming that the amount of the raw amide contained in the reaction product as measured by gas chromatography was reduced below the lower detection limit, successively, while maintaining the same hydrogen introduction rate of 40 L/h (1.35 mol/h per 1 mol of the raw amide compound) but changing the reaction temperature and pressure to 220° C. and normal pressures, respectively, dimethyl amine was additionally introduced to the reaction system at a rate of 6 to 4 L/h (from 0.20 to 0.14 mol/h per 1 mol of the raw amide compound), and the resultant mixture was reacted for 3.5 h. The thus obtained reaction product was subjected to filtration to remove the catalyst therefrom, and then the composition of the thus separated reaction solution was analyzed by gas chromatography. The results are shown in Table 2.

Example 17

The procedure was conducted in the same manner as in Example 10. After confirming that the amount of the raw amide contained in the reaction product as measured by gas chromatography was reduced below the lower detection limit, successively, while maintaining the same hydrogen introduction rate of 40 L/h (1.35 mol/h per 1 mol of the raw amide compound) but changing the reaction temperature and pressure to 220° C. and normal pressures, respectively, dimethyl amine was additionally introduced to the reaction system at a rate of 3 to 2 L/h from 0.10 to 0.07 mol/h per 1 mol of the raw amide compound), and the resultant mixture was reacted for 2.5 h. The thus obtained reaction product was subjected to filtration to remove the catalyst therefrom, and then the composition of the thus separated reaction solution was analyzed by gas chromatography. The results are shown in Table 2.

TABLE 2

| | Introduction of dimethyl amine | Composition of reaction product (mass %) | | | |
| --- | --- | --- | --- | --- | --- |
| | | DMLA*1 | LA*2 | DLMA*3 | others |
| Example 12 | BT*4 | 87.4 | 7.3 | 2.6 | 2.2 |
| | AT*5 | 93.0 | 0.9 | 4.3 | 1.8 |
| Example 13 | BT*4 | 86.7 | 8.6 | 2.1 | 2.5 |
| | AT*5 | 94.2 | 0.7 | 2.8 | 2.3 |
| Example 14 | BT*4 | 87.2 | 6.5 | 3.9 | 1.8 |
| | AT*5 | 93.3 | 0.8 | 4.7 | 1.2 |
| Example 15 | BT*4 | 89.6 | 6.4 | 2.1 | 1.9 |
| | AT*5 | 94.4 | 0.9 | 2.5 | 2.2 |
| Example 16 | BT*4 | 85.4 | 6.9 | 3.8 | 3.9 |
| | AT*5 | 90.4 | 1.0 | 4.1 | 4.5 |
| Example 17 | BT*4 | 86.0 | 7.0 | 3.9 | 3.1 |
| | AT*5 | 91.4 | 0.8 | 4.3 | 3.5 |

Note
*1DMLA = Dimethyl lauryl amine;
*2LA = Lauryl alcohol;
*3DLMA = Dilauryl methyl amine;
*4BT = Before the treatment;
*5AT = After the treatment Comparative Example 3

A rotary autoclave was charged with 300 g of N,N-dimethyl lauroyl amide and a Cu/Cr catalyst "Cu 1800p" commercially available from N.E. Chemcat Corp. An inside of the autoclave was purged with nitrogen, and then hydrogen was introduced thereinto until an inside pressure of the autoclave was increased to 1.5 MPaG. Thereafter, while maintaining the inside pressure of the autoclave at 1.5 MPaG, hydrogen and dimethyl amine were introduced into the reaction system at rates of 40 L/h (1.4 mol/h per 1 mol of the raw amide compound) and from 2 to 1 L/h (from 0.07 to 0.03 mol/h per 1 mol of the raw amide compound), respectively, and the resultant mixture was reacted. The thus obtained reaction product was subjected to filtration to remove the catalyst therefrom, and then the composition of the thus separated reaction solution was analyzed by gas chromatography. As a result, it was confirmed that the content of N,N-dimethyl lauroyl amide in the reaction product was below the lower detection limit, and the reaction product was composed of 82.9% of N,N-dimethyl lauryl amine, 12.4% of N,N-dilauryl methyl amine and 0.6% of lauryl alcohol. Further, it was confirmed that the reaction rate at the time at which 6 hours elapsed from initiation of the reaction was 36.4 [×10$^{-2}$ mol/kg·H)], and the amount of N,N-dimethyl lauryl amine produced when the amount of the raw amide was reduced to 5% was 78.4 (% by mass).

Example 18

The same procedure as in Example 5 was repeated except for using a whole amount of the catalyst separated by filtration and recovered from the reaction product obtained in Example 14. As a result, it was confirmed that the reaction rate upon the above reaction was 57.3 [×10$^{-2}$ mol/(kg·H)], and the amount of N,N-dimethyl lauryl amine produced was 82.9(%). Further, after confirming that the amount of the raw amide contained in the reaction product as measured by gas chromatography was reduced to 0.6% by mass, the same procedure as in Example 14 was successively carried out. The thus obtained reaction product was subjected to filtration to remove the catalyst therefrom, and then the composition of the thus separated reaction solution was analyzed by gas chromatography. The results are shown in Table 3. As a result of analyzing the reaction product by gas chromatography, it was confirmed that the amount of the raw amide contained therein was reduced below the lower detection limit, and the recovered catalyst was free from problems concerning both activity and selectivity even when repeatedly used in the reaction.

TABLE 3

| | Introduction of dimethyl amine | Composition of reaction product (mass %) | | | |
|---|---|---|---|---|---|
| | | DMLA*$^1$ | LA*$^2$ | DLMA*$^3$ | others |
| Example 18 | BT*$^4$ | 87.0 | 6.7 | 3.5 | 2.2 |
| | AT*$^5$ | 93.5 | 0.6 | 4.6 | 1.3 |

Note
*$^1$DMLA = Dimethyl lauryl amine;
*$^2$LA = Lauryl alcohol;
*$^3$DLMA = Dilauryl methyl amine;
*$^4$BT = Before the treatment;
*$^5$AT = After the treatment

The invention claimed is:

1. A process for producing a tertiary amine represented by formula (2):

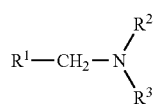

wherein R$^1$ is a linear or branched aliphatic hydrocarbon group having 5 to 23 carbon atoms; and R$^2$ and R$^3$ are each independently a linear or branched alkyl group having 1 to 6 carbon atoms, said process comprising:

(a) reducing an amide compound represented by formula (1):

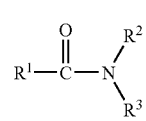

wherein R$^1$, R$^2$ and R$^3$ are the same as defined above, in the presence of a sponge copper catalyst obtained by leaching alloy particles comprising copper and aluminum and drying the thus leached alloy particles.

2. A process according to claim 1, wherein said sponge copper catalyst further comprises at least one element selected from the group consisting of zinc, molybdenum, manganese, magnesium, iron, ruthenium and vanadium.

3. A process according to claim 1, wherein said sponge copper catalyst is obtained by leaching alloy particles comprising copper, aluminum and at least one element selected from the group consisting of zinc, molybdenum, manganese, magnesium, iron, ruthenium and vanadium and drying the thus leached alloy particles.

4. A process according to claim 1, wherein said sponge copper catalyst is obtained by leaching the alloy particles and drying the thus leached alloy particles in an atmosphere of oxygen or air.

5. A process according to claim 1, wherein a content of copper in the sponge copper catalyst is from 20 to 90% by mass in terms of metallic copper.

6. A process according to claim 1, wherein the sponge copper catalyst is present in an amount of from 0.1 to 20% by mass on the basis of the amide compound represented by formula (1).

7. A process according to claim 1, further comprising (b) treating the tertiary amine obtained in said reducing step (a) in the presence of the sponge copper catalyst by introducing a dialkyl amine having a linear or branched alkyl group having 1 to 6 carbon atoms and hydrogen thereinto.

8. A process according to claim 1, wherein said amide compound represented by formula (1) is at least one member selected from the group consisting of N,N -dimethyl caprylamide, N,N-dimethyl 2-ethylhexane amide, N,N-dimethyl caprinamide, N,N -dimethyl lauroyl amide, N,N-dimethyl myristoyl amide, N,N-dimethyl palmitoyl amide, N,N -dimethyl stearoyl amide, N,N-dimethyl isostearoyl amide, N,N-dimethyl oleyl amide, N,N -dimethyl behenyl amide; N,N-diethyl caprylamide, N,N-diethyl 2-ethylhexane amide, N,N -diethyl caprinamide, N,N-diethyl lauroyl amide, N,N-diethyl myristoyl amide, N,N-diethyl palmitoyl amide, N,N-diethyl stearoyl amide, N,N-diethyl isostearoyl amide, N,N-diethyl oleyl amide, N,N-diethyl behenyl amide; N,N-dipropyl caprylamide, N,N-dipropyl 2-ethylhexane amide, N,N-dipropyl caprinamide, N,N-dipropyl lauroyl amide, N,N-dipropyl myristoyl amide, N,N-dipropyl palmitoyl amide, N,N-dipropyl stearoyl amide, N,N-dipropyl isostearoyl amide, N,N-dipropyl oleyl amide, N,N-dipropyl behenyl amide; N-ethyl-N -methyl caprylamide, N-ethyl-N-methyl 2-ethylhexane amide, N-ethyl-N-methyl caprinamide, N-ethyl-N-methyl lauroyl amide, N-ethyl-N-methyl myristoyl amide, N-ethyl-N-methyl palmitoyl amide, N-ethyl-N-methyl stearoyl amide, N-ethyl-N-methyl isostearoyl amide, N-ethyl-N-methyl oleyl amide, N-ethyl-N-methyl behenyl amide; N-methyl-N-propyl caprylamide, N-methyl-N-propyl 2-ethylhexane amide, N-methyl-N-propyl caprinamide, N-methyl-N-propyl lauroyl amide, N-methyl-N-propyl myristoyl amide, N-methyl-N-propyl palmitoyl amide, N-methyl-N-propyl 1 stearoyl amide, N-methyl-N-propyl isostearoyl amide, N-methyl-N-propyl oleyl amide, N-methyl-N-propyl behenyl amide; N-ethyl-N-propyl caprylamide, N-ethyl-N-propyl 2-ethylhexane amide, N-ethyl-N-propyl caprinamide, N-ethyl-N-propyl lauroyl amide, N-ethyl-N-propyl myristoyl amide, N-ethyl-N-propyl palmitoyl amide, N-ethyl-N-propyl 1 stearoyl amide, N-ethyl-N-propyl isostearoyl amide, N-ethyl-N-propyl oleyl amide, N-ethyl-N-propyl behenyl amide, and a mixture thereof.

9. A process according to claim 1, wherein said drying is conducted at a temperature of 60 to 500° C.

10. A process according to claim 1, wherein said drying is conducted at a temperature of 100 to 400° C.

11. A process according to claim 1, wherein said reducing is carried out at a temperature of about 140 to about 300° C.

12. A process according to claim 1, wherein said reducing is carried out at a temperature of 160 to 280° C.

13. A process according to claim 1, wherein said reducing is carried out at a temperature of 180 to 270° C.

14. A process according to claim 1, wherein said reducing is carried out with a hydrogen flow rate of 0.1 to 15 mol/h per 1 mol of said amide compound represented by formula (1).

15. A process according to claim 1, wherein said reducing is carried out with a hydrogen flow rate of 0.3 to 10 mol/h per 1 mol of said amide compound represented by formula (1).

16. A process according to claim 1, wherein said reducing is carried out with a hydrogen flow rate of 0.5 to 5 mol/h per 1 mol of said amide compound represented by formula (1).

17. A process according to claim 1, wherein said reducing is carried out at a pressure of from atmospheric pressure to about 25 MPaG.

18. A process according to claim 1, wherein said reducing is carried out at a pressure of 0.1 to 10 MPaG.

19. A process according to claim 1, wherein said reducing is carried out at a pressure of 0.1 to 5 MPaG.

* * * * *